United States Patent [19]

Baichwal et al.

[11] Patent Number: 5,169,639
[45] Date of Patent: Dec. 8, 1992

[54] CONTROLLED RELEASE VERAPAMIL TABLETS

[75] Inventors: Anand R. Baichwal, Wappingers Falls, N.Y.; John N. Staniforth, Bath, England

[73] Assignee: Edward Mendell Co., Inc., Patterson, N.Y.

[21] Appl. No.: 736,031

[22] Filed: Jul. 25, 1991

Related U.S. Application Data

[63] Continuation-in-part of Ser. No. 491,189, Mar. 9, 1990, Pat. No. 5,128,143, which is a continuation-in-part of Ser. No. 246,368, Sep. 19, 1988, Pat. No. 4,994,276.

[51] Int. Cl.⁵ .......................... A61K 9/22; A61K 9/26; A61K 9/34
[52] U.S. Cl. .................... 424/468; 424/439; 424/464; 424/465; 424/469; 424/470; 424/485; 424/488; 424/499; 424/500; 514/77; 514/780; 514/960; 514/965
[58] Field of Search .............. 424/488, 489, 499, 500, 424/464, 468, 469, 470

[56] References Cited

U.S. PATENT DOCUMENTS

| | | | |
|---|---|---|---|
| 2,993,836 | 7/1961 | Nash et al. | 167/82 |
| 3,074,852 | 1/1963 | Mayron | 167/82 |
| 3,079,303 | 2/1963 | Raff et al. | 167/82 |
| 3,133,863 | 5/1964 | Tansey | 424/465 |
| 3,147,187 | 9/1964 | Playfair | 167/82 |
| 3,388,041 | 6/1968 | Gans et al. | 167/82 |
| 3,456,049 | 7/1969 | Hotko et al. | 424/22 |
| 3,627,583 | 12/1971 | Troy et al. | 127/29 |
| 3,629,393 | 12/1971 | Nakamoto | 424/22 |
| 3,639,169 | 12/1971 | Broeg et al. | 167/82 |
| 3,726,690 | 4/1973 | Schuppner, Jr. | 99/139 |
| 3,728,445 | 1/1973 | Bardani | 424/22 |
| 3,773,920 | 11/1973 | Nakamoto et al. | 424/19 |
| 3,836,618 | 9/1974 | Stevens | 264/101 |
| 3,864,469 | 2/1975 | Reiser et al. | 424/22 |
| 3,950,508 | 4/1976 | Mony et al. | 424/19 |
| 3,963,832 | 6/1970 | Hashimoto et al. | 424/49 |
| 4,013,820 | 3/1977 | Farhadieh et al. | 536/64 |
| 4,072,535 | 8/1977 | Short et al. | 424/22 |
| 4,167,558 | 9/1979 | Sheth et al. | 424/22 |
| 4,199,560 | 4/1980 | Gyarmati | 424/459 |
| 4,259,314 | 3/1981 | Lowey | 424/19 |
| 4,308,251 | 12/1981 | Dunn et al. | 424/19 |
| 4,361,545 | 11/1982 | Powell et al. | 127/29 |
| 4,389,393 | 10/1983 | Schor et al. | 424/19 |
| 4,424,235 | 1/1984 | Sheth et al. | 424/22 |

(List continued on next page.)

FOREIGN PATENT DOCUMENTS

| | | |
|---|---|---|
| 0180364 | 5/1986 | European Pat. Off. |
| 0234670 | 9/1987 | European Pat. Off. |
| 8400104 | 8/1984 | PCT Int'l Appl. |
| 8700044 | 1/1987 | PCT Int'l Appl. |
| 8705212 | 4/1987 | PCT Int'l Appl. |
| 1097207 | 12/1967 | United Kingdom |
| 2178658 | 2/1987 | United Kingdom |
| 2188843 | 10/1987 | United Kingdom |

OTHER PUBLICATIONS

H. M. Ingani et al., 6th. Pharmaceutical Technology Conference, vol. II, pp. 459–460, Canterbury, England, 1987.
Satiaxane Food-Grade Xanthan Gum published by Satia.
Hydrocolloids a publication by Mero Rousselot Satia.
Xanthan Gum/Keltrol Kelzan a Natural Biopolysaccharide for Scientific Water Control.
Formulating for Controlled Release with Methocel Cellulose Ethers, the Dow Chemical Company, 1987.
Pharm. Ind., vol.42, No. 6, 1980, Georgakopoulos et al., "Locust Bean Gum as Granulating and Binding Agent for Tablets".

Primary Examiner—Thurman K. Page
Assistant Examiner—James M. Spear
Attorney, Agent, or Firm—Steinberg & Raskin

[57] ABSTRACT

Controlled release verapamil tablets are disclosed. The tablets include an excipient having a hydrophilic material, preferably containing a mixture of xanthan gum/locust bean gum, and an inert diluent.

9 Claims, 4 Drawing Sheets

U.S. PATENT DOCUMENTS

| | | | |
|---|---|---|---|
| 4,439,453 | 6/1984 | Vogel | 424/22 |
| 4,525,345 | 6/1985 | Dunn et al. | 424/22 |
| 4,542,011 | 9/1985 | Gleixner | 424/16 |
| 4,556,678 | 12/1985 | Hsiao | 514/652 |
| 4,590,062 | 5/1986 | Jang | 424/19 |
| 4,623,394 | 11/1986 | Nakamura et al. | 106/122 |
| 4,692,337 | 9/1987 | Ukigaya et al. | 424/469 |
| 4,695,463 | 9/1987 | Yang et al. | 424/440 |
| 4,695,467 | 9/1987 | Uemura et al. | 424/502 |
| 4,698,101 | 10/1987 | Koivurinta | 424/453 |
| 4,698,264 | 6/1987 | Steinke | 424/408 |
| 4,704,285 | 11/1987 | Alderman | 424/468 |
| 4,717,713 | 1/1988 | Zatz et al. | 514/2 |
| 4,755,389 | 1/1988 | Jones et al. | 514/2 |
| 4,762,702 | 8/1988 | Gergely et al. | 424/300 |
| 4,792,452 | 12/1988 | Howard et al. | 424/475 |
| 4,803,077 | 2/1989 | Mitsuhashi et al. | 424/440 |
| 4,828,836 | 5/1989 | Elger | 424/419 |
| 4,829,056 | 5/1989 | Sugden | 424/464 |
| 4,855,143 | 8/1989 | Lowey | 424/468 |

CONTROLLED RELEASE VERAPAMIL TABLETS

BACKGROUND OF THE INVENTION

This is a continuation-in-part application of U.S. application Ser. No. 07/491,189, filed Mar. 9, 1990, U.S. Pat. No. 5,128,143 which is a continuation-in-part application of U.S. Ser. No. 246,368, filed Sep. 19, 1988, U.S. Pat. No. 4,994,276.

Many attempts have been made in the pharmaceutical art to provide a method by which therapeutically active medicaments can be directly tableted or mixed with a direct compression vehicle and thereafter directly tableted.

Very few therapeutically active medicaments can be directly tableted due to unacceptable flow characteristics and compressible factors of the crystalline or powdered medicament, and also due to the small amounts of medicament needed to provide the desired effect. Therefore, it is a common practice to use an inert ingredient, i.e. excipients, diluents, fillers, binders and the like, such that the combination of the same with the medicament provides a material which can be directly compressed into tablets. In order to provide a directly compressible product, these excipients must have certain physical properties, including flowability, sufficient particle size distribution, binding ability, acceptable bulk and tap densities, and acceptable dissolution properties in order to release the medicament upon oral administration.

U.S. Pat. No. 3,639,169 (Broeg, et al.) discloses one such direct compression vehicle for a therapeutically active medicament which consists of an insoluble or soluble diluent such as lactose dispersed in a matrix of hydrophilic hydratable high polymer such as hydrophilic polysaccharides, hydrocolloids or proteinaceous materials. The polymer, diluent and water are mixed and the resulting dispersion is dried, forming a film. The cooled film is fragmented, ground to the desired particle size and then blended with a desired medicament.

In another method disclosed in U.S. Pat. No. 3,079,303 (Raff, et al.), a granular excipient for making tablets is prepared by spray drying a slurry of 50-98% filler, 1-50% disintegrant, and 1-50% binder. A medicament is then added to the excipient and the finished product is tableted.

It has become desirable to provide pharmaceutical formulations which utilize slow release profiles, an objective not contemplated in Broeg, et al., Raff, et al. or other similar prior art. The advantages of slow release products are well known in the pharmaceutical field and include the ability to maintain a desired blood level over a longer period of time while increasing patient compliance by reducing the number of administrations necessary to achieve the same.

Slow release excipients have been developed which attain their goals by a wide variety of methods. For instance, U.S. Pat. No. 3,629,393 (Nakamoto) utilizes a three-component system to provide slow release tablets in which granules of an active ingredient with a hydrophobic salt of a fatty acid and a polymer are combined with granules of a hydrocolloid and a carrier and granules of a carrier and an active or a buffering agent and then directly compressed into tablets. U.S. Pat. No. 3,728,445 (Bardani) discloses slow release tablets formed by mixing an active ingredient with a solid sugar excipient, granulating the same by moistening with a cellulose acetate phthalate solution, evaporating the solvent, recovering the granules and compressing under high pressure. These disclosures concentrate their attention to the type and combination of polymers and/or gums used, and processes for mixing the same, and therefore have not provided a directly compressible form of gums/polymers and adjuvants which can be used for a wide range of medicaments.

Other slow release excipients are disclosed in the prior art which are directed to particular therapeutically active medicaments.

In one such disclosure, U.S. Pat. No. 3,456,049, (Hotko, et al.), a slow release benzothiadiazine diuretic tablets are prepared by mixing a fatty substance such as hydrogenated vegetable oil, alginic acid, a granulating liquid, a potassium salt and the benzothiadiazine. The wet mass is screened, dried and then compressed into tablets. Similarly, U.S. Pat. No. 4,692,337 (Ukigaya, et al.) provides a slow release excipient for theophylline which utilizes 5–200 parts of ethyl cellulose for each 100 parts theophylline, and optionally contains a filler such as lactose or a lubricant. The ingredients are mixed and compression molded into tablets. In yet another example, U.S. Pat. No. 4,308,251 (Dunn, et al.) a sustained release controlling agent (cellulose acetate phthalate) and 1.0–7.5 percent of an erosion-promoting agent (corn starch) by weight per tablet. A wet granular mass is formed, dried, reduced in particle size and compressed into tablets.

More recently, a great deal of attention in the pharmaceutical field has turned to the use of various hydrocolloid materials such as hydroxypropylmethyl cellulose in providing a slow release matrix for a variety of medicaments.

For example, U.S. Pat. No. 4,389,393 (Schor, et al.) describes a slow release carrier base material of one or more hydroxypropylmethyl celluloses and up to 30% by weight of a mixture of methylcellulose and up to 30% by weight of a mixture of methylcellulose, sodium carboxymethylcellulose and/or cellulose either which can be mixed with a medicament and other needed ingredients such as binders, lubricants, etc. and then tableted. At least one of the hydroxypropylmethyl celluloses must have a methyoxy content of 16–24% by weight, a hydroxypropyl content of 4–32% by weight, and a number average molecular weight of at least 50,000. The carrier base constitutes less than about one third of the weight of the solid unit dosage form.

It is acknowledged in Schor, et al. that in order to make tablets using this carrier base, other ingredients which are conventional in tablet making must necessarily be included, such as binders, fillers, disintegrating agents and the like. Only the completed mixture, which includes these additional ingredients, possess sufficient properties to produce tablets having the necessary hardness and low level of friability. Thus, the carrier base of the Schor, et al. disclosure is not directed to the tableting aspects.

U.S. Pat. No. 4,704,285 (Alderman) discloses solid slow release tablets containing 5–90% hydroxypropyl cellulose ether, 5–75% of an optional additional hydrophilic colloid such as hydroxypropylmethyl cellulose, an effective amount of an active medicament, and optional binders, lubricants, glidants filler, etc. The hydroxypropyl cellulose ether is in the form of a finely sized powder and provides a longer release pattern than identical compositions having coarser particles. However, Alderman acknowledges the necessity of the additional excipients in order to form an acceptable solid tablet, (i.e. fillers, binders, lubricants and glidants). In preferred embodiments, these excipients comprise from 63.5–94% of the tablet.

The carrier bases which provide the slow release profiles in these disclosures can only be compressed into a tablet or a solid dosage form with the aid of other conventional tableting adjuvants such as binders and the like, and therefore contribute only to the slow release aspect of the final solid unit dosage form and not to the tableting aspects. In other words, in each of these disclosures, it is necessary for to first determine the physical properties of the active medicaments to be tableted and thereafter proceed through a series of trial and error experiments in order to determine the optimal amount of gums/polymers and other adjuvants to produce the right formulation which is free flowing and which can be compressed to a slow release solid dosage unit. This procedure is time intensive and costly.

Similarly, slow release excipients disclosed to date which incorporate virtually any synthetic polymer such as hydroxypropylmethylcellulose, methyl cellulose, polyvinylpyrollidone, and any natural gum such as accacia, tragacanth, alginates, chitosan, xanthan, pectin and other to date have been mainly directed to the slow release aspect and do not satisfactorily address the tableting aspect. This is because these materials are not available in the necessary physical form that is essential for forming a solid unit dosage form.

The failure of slow release excipients such as the above to be regarded as to their tableting properties is due, for instance, to their necessarily very fine particle size, which property does not lend itself well to flowability. Also, hydroxypropylmethyl cellulose polymers and the like are not particularly good binding agents, a problem which is amplified when other poorly binding excipients or medicaments are included in a formulation. Thus, at higher percentages of such polymers in the final mixture, it becomes difficult if not impossible to provide a good flowing tablet formulation for direct compression without the use of further excipients, and experimentation.

The tableting aspect has been addressed, albeit unsatisfactorily, in U.S. Pat. No. 4,590,062 (Jang). Jang discloses a dry direct compressed slow release tablet containing from 0.01 to 95 parts by weight of an active ingredient combined with a matrix blend of 1–96 parts of a wax, and a fatty acid material or neutral lipid. The tablets can be made by dry blending the active ingredients with the matrix blend and compressing. However, while this combination of ingredients can provide a directly compressible tablet, the formulator is still required to perform a great deal of experimentation to provide the correct release profile for the chosen medicament, given the wide range of wax (used for its binding and compacting properties) which can be included.

It is therefore an object of the present invention to provide a free-flowing directly compressible controlled release excipient which can be used to provide a controlled release verapamil tablet.

It is a further object of the present invention to provide a free-flowing directly compressible slow release excipient which is relatively inexpensive to manufacture due to the lack of coatings and expensive equipment.

It is a further object of the present invention to provide a controlled release verapamil tablet which can be manufactured by mixing verapamil with a premanufactured controlled release excipient to provide a desired dissolution profile.

It is yet another object of the present invention to provide a controlled release tablet comprising verapamil as an active therapeutic agent and a premanufactured controlled release excipient, which, depending upon the method of admixture with verapamil, provides different desireable dissolution profiles.

SUMMARY OF THE INVENTION

In accordance with the above objects and others, the present invention is related to a tablet for the controlled release of verapamil in the gastro-intestinal tract, comprising a hydrophilic material comprising a heteropolysaccharide and a polysaccharide gum capable of cross-linking the heteropolysaccharide in the presence of aqueous solutions, an inert pharmaceutical filler, and an effective amount of verapamil. The ratio of the inert diluent to the hydrophilic gum material is preferably from about 4:1 to about 0.67:1. The ratio of verapamil to the hydrophilic material is preferably from about 3:1 to about 1:3.

In preferred embodiments of the present invention, the heteropolysaccharide comprises a xanthan gum, and the polysaccharide gum comprises locust bean gum.

In certain preferred embodiments of the present invention, the verapamil tablets provide a controlled release product wherein about 50 percent of the verapamil contained in the tablet will dissolve in distilled water within about 2–5 hours if a 4–8 hour dosing preparation is desired.

In a preferred embodiment, the present invention is related to a tablet for the controlled release of verapamil in the gastro-intestinal tract, comprising a controlled release excipient comprising a hydrophilic material comprising about 25 to about 55 percent, and most preferably 30, percent by weight hydrophilic material comprising xanthan gum and locust bean gum in a ratio of about 1:1, and from about 75 to about 45 percent by weight inert diluent; and an effective amount of verapamil. In most preferred embodiments, the ratio of verapamil to the hydrophilic material is from about 1.0:0.4 to about 1.0:0.7.

In certain embodiments of the invention, the verapamil is dry granulated with the controlled release excipient prior to tableting.

In other embodiments of the present invention, the verapamil is wet granulated with the controlled release excipient prior to tableting.

In yet other embodiments of the present invention, a first portion of the verapamil is dry granulated with a first portion of said controlled release excipient, and a second portion of the verapamil is wet granulated with a second portion of the controlled release excipient, the dry granulated portion and the wet granulated portion being combined prior to tableting.

The controlled release verapamil tablets thus formed slowly release verapamil when ingested and exposed to gastric fluids. By varying the amount of excipient relative to verapamil, the amount of excipient relative to inert filler, and the method of admixture of the excipient with verapamil, the controlled release profile of the tablets of the invention can be altered.

DETAILED DESCRIPTION OF THE INVENTION

Figure 1:
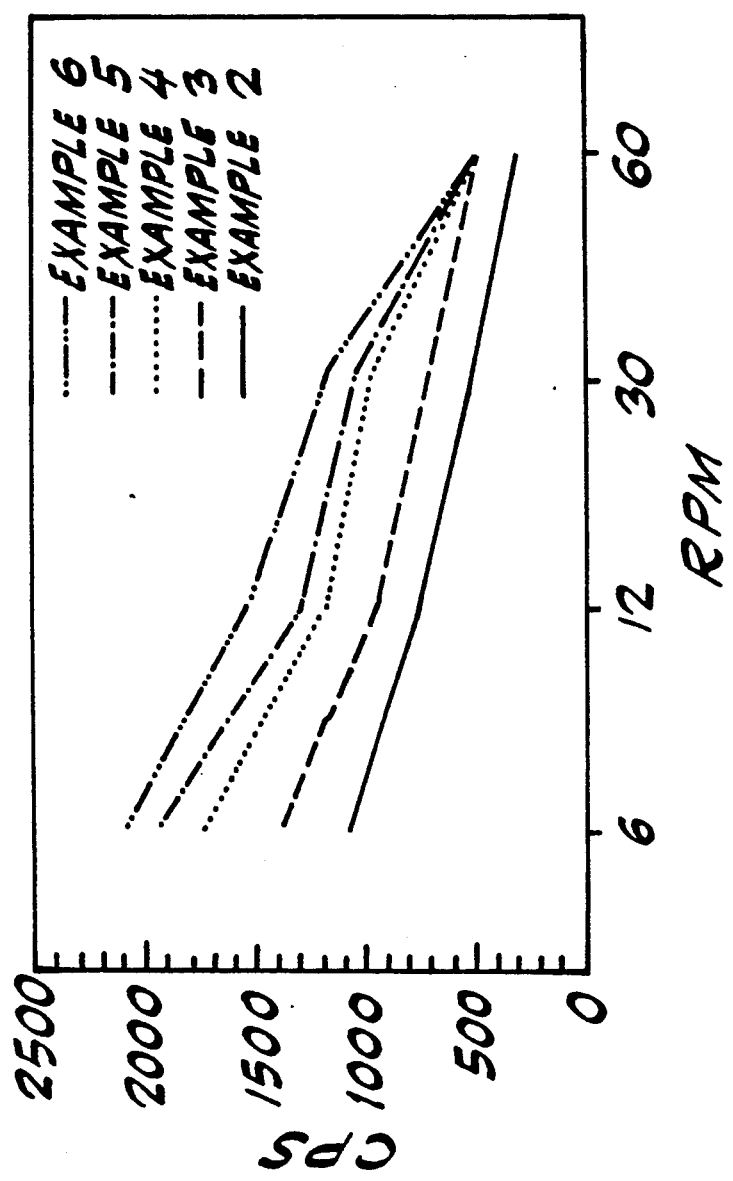
FIG. 1 is a graphical representation of the viscosities of the excipients in Examples 2–6 determined at four different RPM's.

The excipients of the present invention have been preoptimized by providing an excipient product which a may be mixed with a wide range of medicaments and directly compressed into solid dosage forms, without the aid of the usual pharmaceutical dry or wet binders, fillers, disintegrants, glidants etc., which must be added in prior art compositions to obtain an acceptable solid dosage form. Thus, the excipients of the present invention substantially overcome the need for conducting further experimentation needed to optimize release characteristics and tableting properties for a particular therapeutically active medicament.

In other words, the controlled release excipient used in the present invention provides a product which contains a combination of ingredients in preselected proportions to each other which provides a desired controlled/slow release profile for a wide variety of drugs. Thus, once the excipient product is admixed with an active medicament (and preferably with a lubricant) in a ratio to the hydrophilic matrix in accordance with the present invention, the resulting mixture may be directly compressed into solid dosage forms.

Xanthan gum, the preferred heteropolysaccharide, is produced by microorganisms, for instance, by fermentation with the organism xanthomonas compestris. Most preferred is xanthan gum which is a high molecular weight ($>10^6$) heteropolysaccharide. Xanthan gum contains D-glucose, D-mannose, D-glucuronate in the molar ratio of 2.8:2.0:20, and is partially acetylated with about 4.7% acetyl. Xanthan gum also includes about 3% pyruvate, which is attached to a single unit D-glucopyromosyl side chain as a metal It dissolves in hot or cold water and the viscosity of aqueous solutions of xanthan gum is only slightly affected by changes in the pH of a solution between 1 and 11.

Other preferred heteropolysaccharides include derivatives of xanthan gum, such as deacylated xanthan gum, the carboxymethyl ether, and the propylene glycol ester.

The polysaccharide gums used in the present invention which are capable of cross-linking with the heteropolysaccharide include the galactomannans, i.e., polysaccharides which are composed solely of mannose and galactose.

A possible mechanism for the interaction between the galactomannan and the heteropolysaccharide involves the interaction between the helical regions of the heteropolysaccharide and the unsubstituted mannose regions of the galactomannan. Galactomannans which have higher proportions of unsubstituted mannose regions have been found to achieve more interaction with the heteropolysaccharide. Hence, locust bean gum, which has a higher ratio of mannose to the galactose, is especially preferred as compared to other galactomannans such as guar and hydroxypropyl guar.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties. When admixed with an appropriate polysaccharide gum capable of cross-linking with the heteropolysaccharide in accordance with the present invention and exposed to an aqueous solution, gastric fluid, etc., the gums pack closely and many intermolecular attachments are formed which make the structure strong and provide a hydrophilic gum matrix having high gel strength.

Other polysaccharide gums which may or may not cross-link with the heteropolysaccharides of the present invention may also be added to the hydrophilic material in addition such as the alginates, tragacanth, accacia, karaya, agar, pectins, carrageenan, hydroxypropylmethyl cellulose, hydroxypropyl cellulose, carboxymethyl cellulose, polyvinyl pyrrolidone, mixtures thereof, and the like.

Two steps which are generally required for gelation are the fast hydration of the macromolecules which comprise the hydrophilic material and thereafter the association of the molecules to form gels. Thus, two important properties of a hydrophilic gel matrix which are needed for application in a slow release system are the fast hydration of the system and a matrix having a high gel strength. These two important properties which are needed for application in a slow release system are the fast hydration of the system and a matrix having a high gel strength. These two important properties which are necessary to achieve a slow release hydrophilic matrix are maximized in the present invention by the particular combination of materials. In particular, heteropolysaccharides such as xanthan gum have excellent water wicking properties which provide fast hydration. On the other hand, the combination of xanthan gum with polysaccharide materials and the like which are capable of cross-linking the rigid helical ordered structure of the xanthan gum (i.e. with unsubstituted mannose regions in the galactomannans) thereby act synergistically to provide a higher than expected viscosity (i.e., high gel strength) of the matrix.

Certain other polysaccharide gums, including alginic acid derivatives, hydrocolloids, etc. also are believed to act synergistically with xanthan gum to produce matrices having high gel strength. The combination of xanthan gum with locust bean gum with or without the other polysaccharide gums is especially preferred. However, the combination of any polysaccharide gums known to produce a synergistic effect when exposed to aqueous solutions may be used in accordance with the present invention. By synergistic effect, it is meant that the combination of two or more polysaccharide gums produce a higher viscosity and/or faster hydration than that which would be expected by either of the gums alone. One example of a combination of polysaccharide gums which has been reported to exhibit such synergism in food products is kappa carrageenan and a galactomannan such as guar gum and/or locust bean gum. Additionally, the combination of propylene glycol alginate and sodium carboxymethylcellulose has also been reported to exhibit a synergistic effect as a stabilizer in fruit juices in U.S. Pat. No. 4,433,000. This list is not meant to be exclusive, and many other synergistic combinations will be readily apparent to those skilled in the art.

It is also possible that the type of synergism which is present with regard to the heteropolysaccharide/polysaccharide gum combination of the present invention could also occur between two homo- or heteropolysaccharides.

Further information concerning the controlled release excipient used in the present invention is set forth in applicant's U.S. Pat. No. 4,994,276, and applicant's application Ser. No. 07/491,189, filed Mar. 9, 1990, U.S. Pat. No. 5,128,143 both of which are deemed incorporated by reference.

Mixtures of xanthan gum and locust bean gum in a ratio from about 20:1 to about 1:10 are disclosed in U.S. Pat. No. 3,726,690 (Schuppner) as being useful to minimize serum separation in amounts of 0.2-0.6% by weight of acidified food products. In addition, mixtures of xanthan gum/locust bean gum are commercially available as Lygomme H96 from Satia and are recommended for uses such as syrup thickening, suspension of active components and emulsion stabilization.

In the present invention, it has been discovered that the controlled release properties of the tablets are optimized when the ratio of xanthan gum to polysaccharide material (i.e., locust bean gum, etc.) is about 1:1, although xanthan gum in an amount of from about 20 to about 80 percent or more by weight of the hydrophilic material provides an acceptable slow release product.

Upon oral ingestion and contact with gastric fluid, the controlled release tablets prepared according to the present invention swell and gel to form a hydrophilic gel matrix from which the drug is released. The swelling of the matrix causes a reduction in the bulk density of the tablet and provides the buoyancy necessary to allow the gel mass to float on the stomach contents to provide a slow delivery of the medicament. The matrix, the size of which is dependent upon the size of the original tablet, can swell considerably and become obstructed near the opening to the pyrlorus. Since the medicament is dispersed throughout the tablet (and consequently throughout the gel matrix), a constant amount of drug can be released per unit time in vivo by dispersion or erosion of the outer portions of the matrix. This phenomenon is commonly referred to as a zero order release profile or zero order kinetics. The process continues, with the matrix remaining buoyant in the stomach, until substantially all of the medicament is released. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract. Moreover, the chemistry of the ingredients comprising the excipients of the present invention is believed to be similar to certain known muco adhesive substances such as polycarbophil. Muco adhesive properties are desirable for buccal delivery systems. Thus, it may be possible that the gel system could potentially loosely interact with the mucin in the gastrointestinal tract and thereby provide another mode by which a constant rate of delivery of the medicament is achieved. The above hypothesis is included for discussion purposes only and is not intended to limit the scope of the present invention.

These two phenomenons, i.e., buoyancy of the gel matrix and the mucoadhesive properties discussed above, are possible mechanisms by which the gel matrix of the present invention could interact with the mucin and fluids of the gastrointestinal tract and provide a constant rate of delivery of the medicament. Other mechanisms are possible and therefore this hypothesis is not meant to limit the scope of the present invention.

Any generally accepted soluble or insoluble inert pharmaceutical filler (diluent) material can be used. Preferably, the inert pharmaceutical filler comprises a monosaccharide, a disaccharide, a polyhydric alcohol, and/or mixtures thereof. Examples of suitable inert pharmaceutical fillers include sucrose, dextrose, lactose, microcrystalline cellulose, xylitol, fructose, sorbitol, mixtures thereof and the like. However, it is preferred that a soluble pharmaceutical filler such as lactose, dextrose, sucrose, or mixtures thereof be used.

An effective amount of any generally accepted pharmaceutical lubricant, including the calcium or magnesium soaps may be added to the above-mentioned ingredients of the excipient be added at the time the medicament is added, or in any event prior to compression into a said dosage form. Most preferred is magnesium stearate in any amount of about 0.5-3% by weight of the solid dosage form.

The combination of the hydrophilic material (i.e., a mixture of xanthan gum and locust beam gum) with the inert diluent provides a ready to use product in which a formulator need only blend the desired active medicament and an optional lubricant with the excipient and then compress the mixture to form slow release tablets. The excipient may comprise a physical admix of the gums along with a soluble excipient such as compressible sucrose, lactose or dextrose, although it is preferred to granulate or agglomerate the gums with plain (i.e., crystalline) sucrose, lactose, dextrose, etc., to form an excipient. The granulate form has certain advantages including the fact that it can be optimized for flow and compressibility; it can be tableted, formulated in a capsule, extruded and spheronized with an active medicament to form pellets, etc.

The pharmaceutical excipients prepared in accordance with the present invention are preferably subjected to wet granulation before the medicament is added, although the ingredients of the present excipient can be held together by any agglomeration technique to yield an acceptable excipient product. In this technique, the desired amounts of the heterpolysaccharide, the polysaccharide material, and the inert filler are mixed together and thereafter a moistening agent such as water, propylene glycol, glycerol, alcohol or the like is added to prepare a moistened mass. Next, the moistened mass is dried. The dried mass is then milled with conventional equipment into granules. Therefore, the excipient product is ready to use.

The excipient is free-flowing and directly compressible. Accordingly, the excipient may be mixed in the desired proportion with a therapeutically active medicament and optional lubricant (dry granulation). Alternatively, all or part of the excipient may be subjected to a wet granulation with the active ingredient and thereafter tableted. The complete mixture, in an amount sufficient to make a uniform batch of tablets, is then subjected to tableting in a conventional production scale tableting machine at normal compression pressure, i.e. about 2000-1600 lbs/sq in. However, the mixture should not be compressed to such a degree that there is subsequent difficulty in its hydration when exposed to gastric fluid.

One of the limitations of direct compression as a method of tablet manufacture is the size of the tablet. If the amount of active is high a pharmaceutical formulator may choose to wet granulate the active with other excipients to attain a decent size tablet with the right compact strength. Usually the amount of filler/binder or excipients needed in wet granulation is less than that in direct compression since the process of wet granulation contributes to some extent toward the desired physical properties of a tablet.

The average tablet size for round tablets is preferably about 500 mg to 750 mg and for capsule-shaped tablets about 750 mg to 1000 mg.

The average particle size of the granulated excipient of the present invention ranges from about 50 microns to about 400 microns and preferably from about 185 microns to about 265 microns. The particle size of the granulation is not narrowly critical, the important parameter being that the average particle size of the granules, must permit the formation of a directly compressible excipient which forms pharmaceutically acceptable tablets. The desired tap and bulk densities of the granulation of the present invention are normally between from about 0.3 to about 0.8 g/ml, with an average density of from about 0.5 to about 0.7 g/ml. For best results, the tablets formed from the granulations of the present invention are from about 6 to about 8 kg hardness. The average flow of the granulations prepared in accordance with the present invention are from about 25 to about 40 g/sec.

The ratio of medicament to the hydrophilic material is based in part upon the relatively solubility of the medicament and the desired rate of release. For instance, the ratio of medicament to hydrophilic material can be adjusted to yield a product wherein 50 percent of the medicament will dissolve in distilled water within about 3.5-5 hours if a 6-8 hour dosing preparation is desired. This is accomplished by providing a ratio of medicament to hydrophilic material of about 1:3-7 for a wide range of medicaments of varying solubilities. However, it would be obvious to one skilled in the art that by varying this proportion and/or the total weight of the tablet, etc., one can achieve different slow release profiles, and may extend the dissolution of some medicaments to about 24 hours.

Variables which may affect the release rate and the compressibility of tablets prepared with the excipient of the present invention are the drug to polymer ratio; the method of incorporation of excipient (method of granulation); the relative amount of the gum blend; and the composition of gum mix.

DETAILED DESCRIPTION OF THE PREFERRED EMBODIMENTS

The following examples illustrate various aspects of the present invention. They are not to be construed to limit the claims in any manner whatsoever.

EXAMPLE 1

Preparation of Excipient

A controlled release excipient according to the present invention is prepared as follows. First, 600 g of sucrose and 300 g of a mixture of xanthan gum and locust bean gum in approximately a 1:1 ratio, all in powder form having an average particle size of less than about 50 microns, are blended for two minutes in a granulator (i.e., a high speed mixer having a combination chopper/impeller). About 125 ml of water is added to the mixture until there is a sharp rise in the power consumed (about 2-3 minutes). The mixed product, which is now in the form of granules, is removed from the granulator and dried in a convection air-oven for 24 hours at a temperature of about 40°-60° C. The dried granulation is then passed through a 20 mesh screen. The product is now ready to be used as a slow release excipient which is suitable for direct compression with any active medicament to form a slow release tablet.

EXAMPLES 2-6

Gum/Total Excipient

Controlled release excipients are prepared according to procedures set forth in Example 1. The excipients of Examples 2-6 each include dextrose as the inert pharmaceutical filler, and xanthan gum/locust bean gum in a 1:1 ratio. The percentage of gums as compared to the total weight of the excipient in Examples 2-6 are 30%, 40%, 50%, 60% and 70%, respectively. The viscosities of the excipients are then determined at four different RPM's using a #2 spindle on a Brookfield viscometer. The results are shown in FIG. 1. As can be seen from the graph, the viscosity increases as the percentage of gum included in the excipient increases.

EXAMPLE 7

Preparation of Excipient

A controlled release excipient according to the present invention is prepared as follows. First, 630 g of dextrose and 270 g of a hydrophilic material comprising 135 g of xanthan gum and 135 g of locust bean gum, all in a powder form having an average particle size of less than 50 microns are blended for two minutes in a granulator (i.e., a high speed mixer having a combination chopper/impeller). After pre-mixing, 100 ml of water is added until there is sharp rise in the power consumption (about 2-3 minutes). The mixed product, which is now in the form of granules, is removed from the granulator and dried in a convection air-oven for 24 hours at a temperature of about 40°-60° C. The dried granulation is then passed through a 20 mesh screen. The product is now ready to be granulated with an active, the result of which is suitable for compression to form a slow release tablet.

EXAMPLE 8

Wet Granulation

Verapamil HCl is a relatively soluble active ingredient which has a dose of about 240 mg in a sustained release tablet form.

In Example 8 the active ingredient (Verapamil) is granulated with the controlled release excipient as follows. The excipient of Example 7 (385 g) is first blended with 115 g Verapamil HCl for two minutes in a granulator. After premixing, about 90 ml of water is added until there is a sharp rise in the power consumed by the granulator (about 2-3 minutes). The mixed product, which is now in the form of granules, is removed from the granulator and dried in a convection air-oven for 24 hours at a temperature of about 40°-60° C. The dried granulation is then passed through a 20 mesh screen. The final composition of the mixture is about 77.0% of the excipient of Example 7, and 23.0% of Verapamil HCl.

The mixture is blended with hydrogenated vegetable oil for about 5 minutes in a V-blender. Magnesium stearate is then added and the mixture is blended for an additional 5 minutes. The final composition of the mixture is about 75.0% of the excipient of Example 7, 22.5% Verapamil HCl, 2.00% hydrogenated vegetable oil, and 0.500% magnesium stearate, by weight. The mixture is then compressed on a Stokes RB-2 rotary tablet press with sixteen stations. The average weight of the tablets produced is about 1067 mg and the crushing strength about 7-8 kgs. Each tablet contains about 240.08 Verapamil, 800.25 mg excipient of Example 7, 21.34 mg hydrogenated vegetable oil, and 5.34 mg magnesium stearate.

EXAMPLE 9

Dry Granulation

The active ingredient is directly compressed with the controlled release excipient of Example 7 to form sustained release tablets having approximately the same composition as those of Example 8 as follows. 300 g of the excipient of Example 7 is first blended with 90 g Verapamil HCl for 10 minutes in a V-blender. Hydrogenated vegetable oil is then added and the mixture is blended for 5 minutes. Magnesium stearate is then added and the mixture is blended for an additional 5 minutes. The final composition of the mixture is the same as in Example 8 and is tableted.

EXAMPLE 10

Mixed Granulation

The active ingredient is granulated with 50% of the controlled release excipient as follows. Half of the excipient of Example 7 is first blended with Verapamil HCl for 2 minutes in a granulator. Next, about 75 ml of water is added until there is a sharp rise in power consumed (usually 2-3 minutes). The mixed product, which is now in the form of granules, is removed from the granulator and dried in a convection air-oven for 24 hours at a temperature of about 40°-60° C. The dried granulation is then passed through a 20 mesh screen. The final composition is about 62.5% of the excipient of Example 7 and about 37.5% Verapamil HCl. The mixture is then blended with other half of excipient of Example 7 for 10 minutes in V-blender. Hydrogenated vegetable oil is then added and blended 5 minutes, magnesium stearate is then added and blended for an additional 5 minutes. The final composition of the mixture is then same as in Example 8 and Example 9 and is tableted.

EXAMPLES 11-13

Effect of Method of Incorporation

In Examples 11-13, the active ingredient (Verapamil HCl) is granulated with the controlled release excipient according to the methods set forth in Examples 7-9, respectively, in order to compare the dissolution curves obtained.

In Example 11, the excipient is prepared according to the process set forth in Example 7 and is then blended with the active ingredient and tableted according to the process set forth in Example 8. In Example 12, the excipient is prepared according to the process set forth in Example 7 and is then blended with the active ingredient and tableted, according to the process set forth in Example 9. In Example 13, the excipient is prepared according to the process set forth in Example 7 and is then blended with the active ingredient and tableted according to the process set forth in Example 10.

In each of Examples 11-13, the tablets weigh about 1067 mg. The drug:gum ratio in each of Examples 11-13 is 1:1; and the locust bean gum (LBG) to xanthan gum (XG) ratio is 1:1.

Each tablet of Examples 11-13 contain about 240 mg Verapamil HCl, about 800 mg excipient, about 21.3 mg hydrogenated vegetable oil, and about 5.3 mg magnesium stearate. Further information regarding Examples 11-13 is provided in Table 1 below.

TABLE 1

| Example | Drug:Gum Ratio | % Gum in Excipient | LBG:XG Ratio | T50 | T90 |
|---------|----------------|--------------------|--------------|-----|-----|
| 11      | 1:1            | 35                 | 1:1          | 3.7 | 16.5 |
| 12      | 1:1            | 35                 | 1:1          | 1.0 | 4.5 |
| 13      | 1:1            | 35                 | 1:1          | 2.4 | —   |

Figure 2:
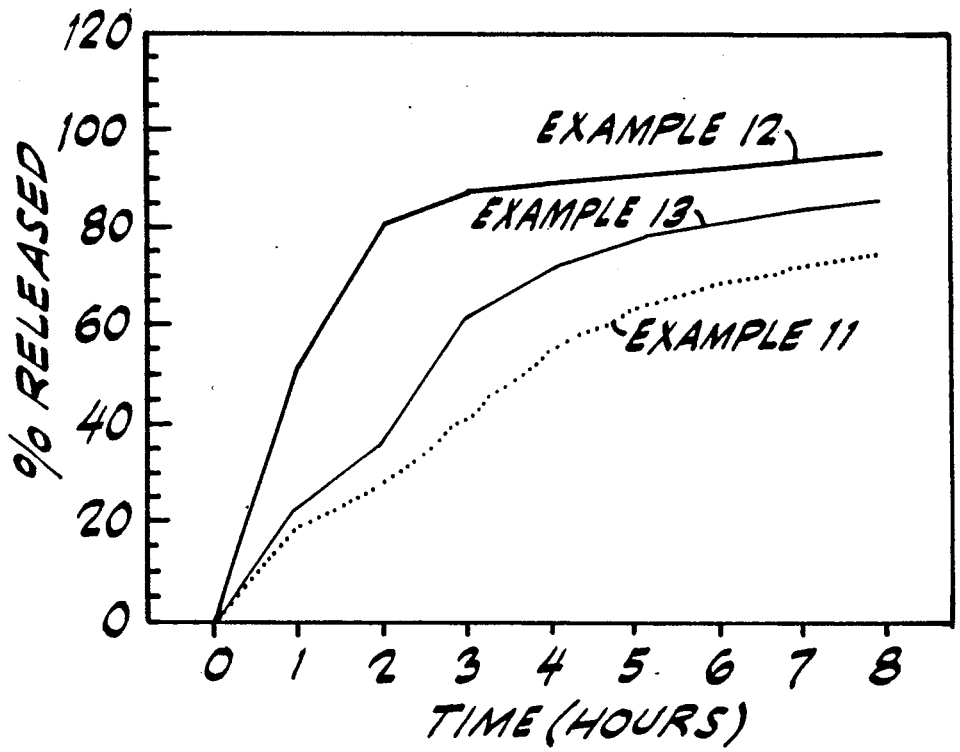
FIG. 2 is a graphical representation of the dissolution curves provided by Examples 11–13.

The tablets are tested in an automated USP dissolution apparatus, using distilled water at a volume of 1 liter and paddle method at 50 R.P.M. At 30 minute intervals the ultraviolet absorbance of filtered portions of solution are compared to a standard having a known concentration of USP Verapamil HCl in the same medium. The results are provided in FIG. 2.

EXAMPLES 14-16

Effect of Amount of Gum in Excipient

In Examples 14-16, the amount of gum in the excipient is varied in order to compare the dissolution curves of the active ingredient (Verapamil HCl) obtained.

In each of Examples 14-16, the controlled release excipient is prepared according to the process set forth in Example 7, except that the amount of gum in the excipient is varied. The slow release excipient obtained for each of Examples 14-16 is then blended with the active ingredient and tableted according to the method set forth in Example 10.

The tablets of Example 14 weigh about 861.5 mg and contain about 240 mg Verapamil HCl, about 600 mg excipient, about 17.2 mg hydrogenated vegetable oil, and about 4.3 mg magnesium stearate. The tablets of Example 15 weigh about 949.70 mg and contain about 240 mg Verapamil HCl, about 686 mg excipient, about 19 mg hydrogenated vegetable oil, and about 4.70 mg magnesium stearate. The tablets of Example 16 weigh about 1066.60 mg and contain about 240 mg Verapamil HCl, about 800 mg excipient, about 21.3 mg hydrogenated vegetable oil, and about 5.3 mg magnesium stearate. Further information regarding Examples 14-16 is provided in Table 2 below.

TABLE 2

| Example | Drug:Gum Ratio | % Gum in Excipient | LBG:XG Ratio | T50 | T90 |
|---------|----------------|--------------------|--------------|-----|-----|
| 14      | 1:1            | 40                 | 1:1          | 2.9 | —   |
| 15      | 1:1            | 35                 | 1:1          | 2.4 | —   |
| 16      | 1:1            | 30                 | 1:1          | 1.2 | 3.3 |

Figure 3:
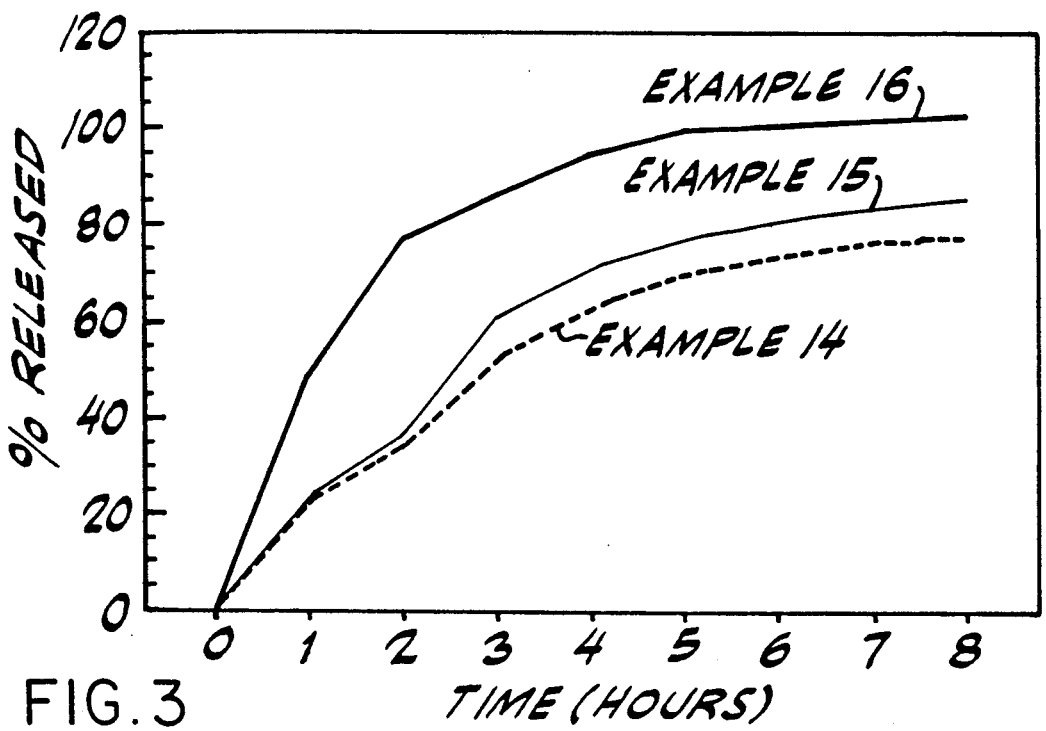
FIG. 3 is a graphical representation of the dissolution curves provided by Examples 14–16.

The tablets are then tested for dissolution in the same manner as in Examples 11-13. The results are provided in FIG. 3.

EXAMPLES 17-20

LBG:XG Ratio

In Examples 17-20, the ratio of locust bean gum (LBG) to xanthan gum (XG) is varied and the dissolution curves compared.

In each of Examples 17-20, the controlled release excipient is prepared according to the process set forth in Example 7, except that the LBG:XG ratio is varied. The controlled release excipient obtained for each of Examples 17-20 is then blended with the active ingredient (Verapamil HCl) and tableted according to the process set forth in Example 10.

Each of the tablets of Examples 17-20 contain about 240 mg Verapamil HCl, about 738 mg excipient, about 20 mg hydrogenated vegetable oil, and about 50 magnesium stearate. Further information regarding Examples 17-20 is provided in Table 3 below:

TABLE 3

| Example | Drug:Gum Ratio | % Gum in Excipient | LBG:XG Ratio | T50 | T90 |
|---|---|---|---|---|---|
| 17 | 1:1 | 32.5 | 55:45 | 0.9 | 5.0 |
| 18 | 1:1 | 32.5 | 60:40 | 0.3 | 0.5 |
| 19 | 1:1 | 32.5 | 1:1 | 2.7 | 11.5 |
| 20 | 1:1 | 32.5 | 25:75 | 4.8 | 17.5 |

Figure 4:
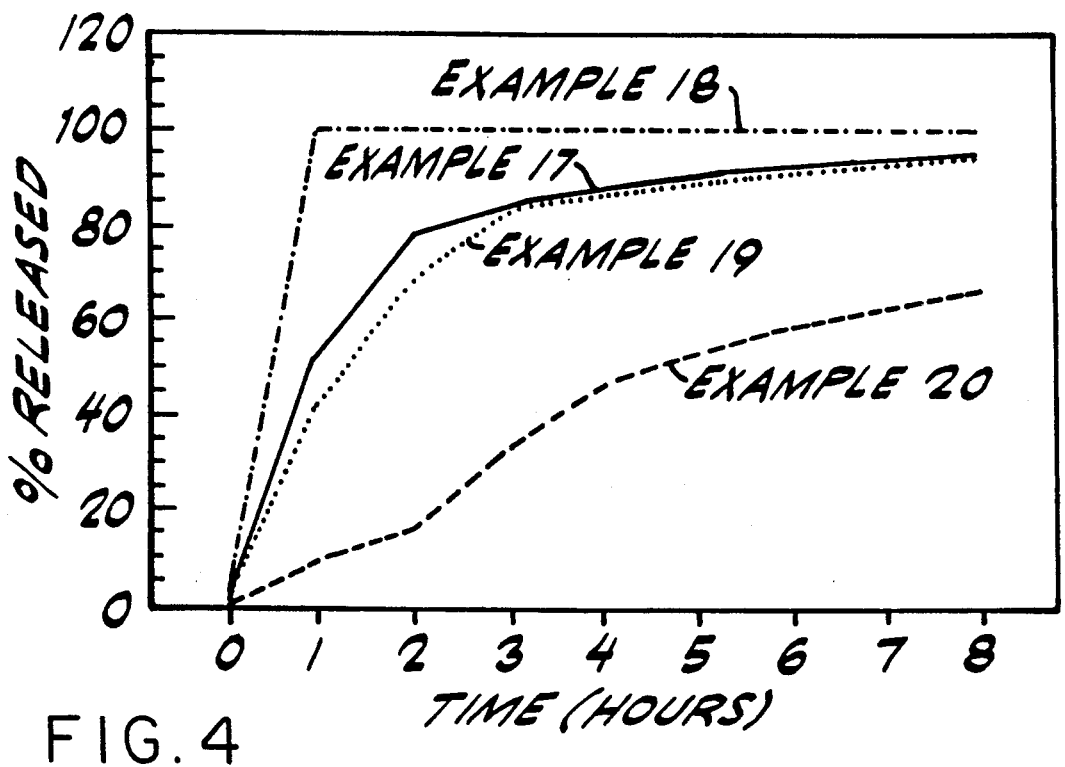
FIG. 4 is a graphical representation of the dissolution curves provided by Examples 17–20.

The tablets are then tested for dissolution in the same manner as in Examples 11-13. The results are provided in FIG. 4.

EXAMPLES 21-23

Drug:Gum Ratio

In Examples 21-23, the drug to gum ratio is varied and the dissolution curves compared.

In each of Examples 21-23, the slow release excipient is prepared according to Example 7 and is then blended with the active ingredient (Verapamil HCl) and tableted.

In Example 21, the tablets contain about 240 mg Verapamil, about 240 mg excipient, about 9.84 mg hyrogenated vegetable oil, and about 2.6 mg magnesium stearate. In Example 22, the tablets contain about 240 mg verapamil, about 480 mg excipient, about 14.8 mg hydrogenated vegetable oil, and about 3.7 mg magnesium stearate. In Example 23, the tablets contain about 120 mg Verapamil, about 720 mg excipient, about 17.2 mg hydrogenated vegetable oil, and about 4.3 mg magnesium stearate. Further information regarding Examples 21-23 is set forth in Table 4 below:

TABLE 4

| Example | Drug:Gum Ratio | % Gum in Excipient | LBG:XG Ratio | T50 | T90 |
|---|---|---|---|---|---|
| 11 | 2:1 | 50 | 1:1 | 0.4 | 0.9 |
| 12 | 1:1 | 50 | 1:1 | 5.5 | — |
| 13 | 1:3 | 50 | 1:1 | — | — |

Figure 5:
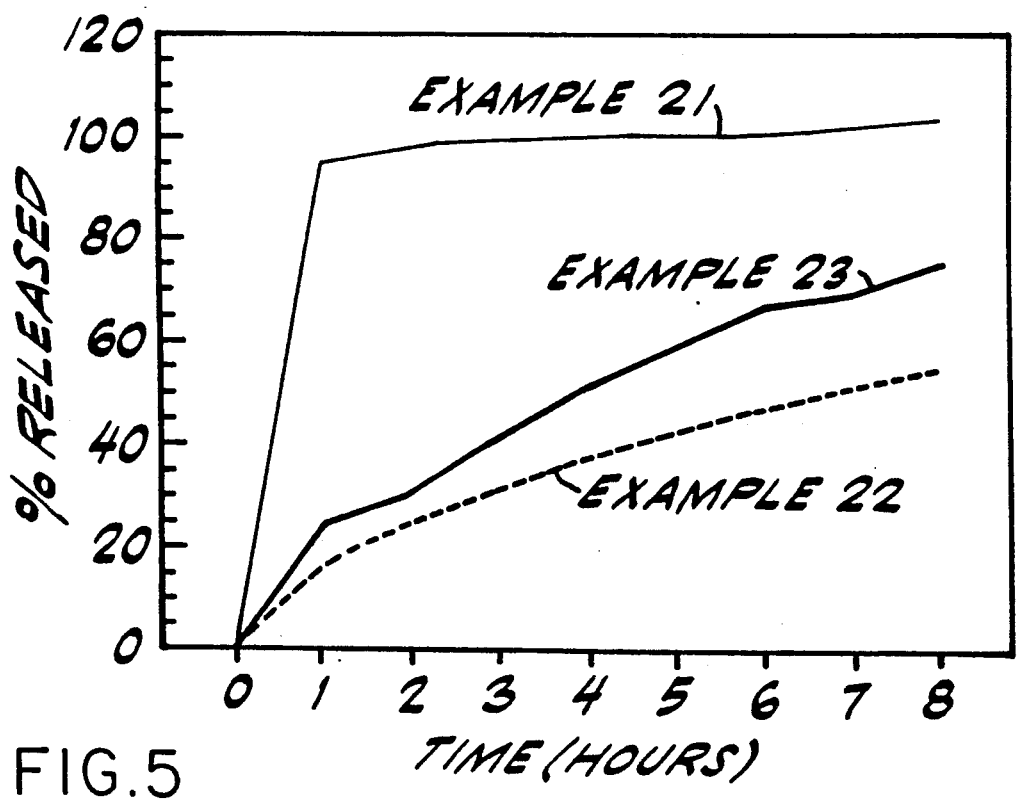
FIG. 5 is a graphical representation of the dissolution curves provided by Examples 21–23.

The tablets are then tested for dissolution in the same manner as in Examples 11-13. The results are provided in FIG. 5.

EXAMPLE 24

Tailoring to a Known Dissolution Curve

By varying the amount of gum, the LBG:XG ratio, the method of incorporation, or the drug:gum ratio, it is possible to closely match the dissolution profile of a different slow release formulation of the same drug. This is demonstrated in the following example.

First, a controlled release excipient is prepared according to the process set forth in Example 7.

Figure 6:
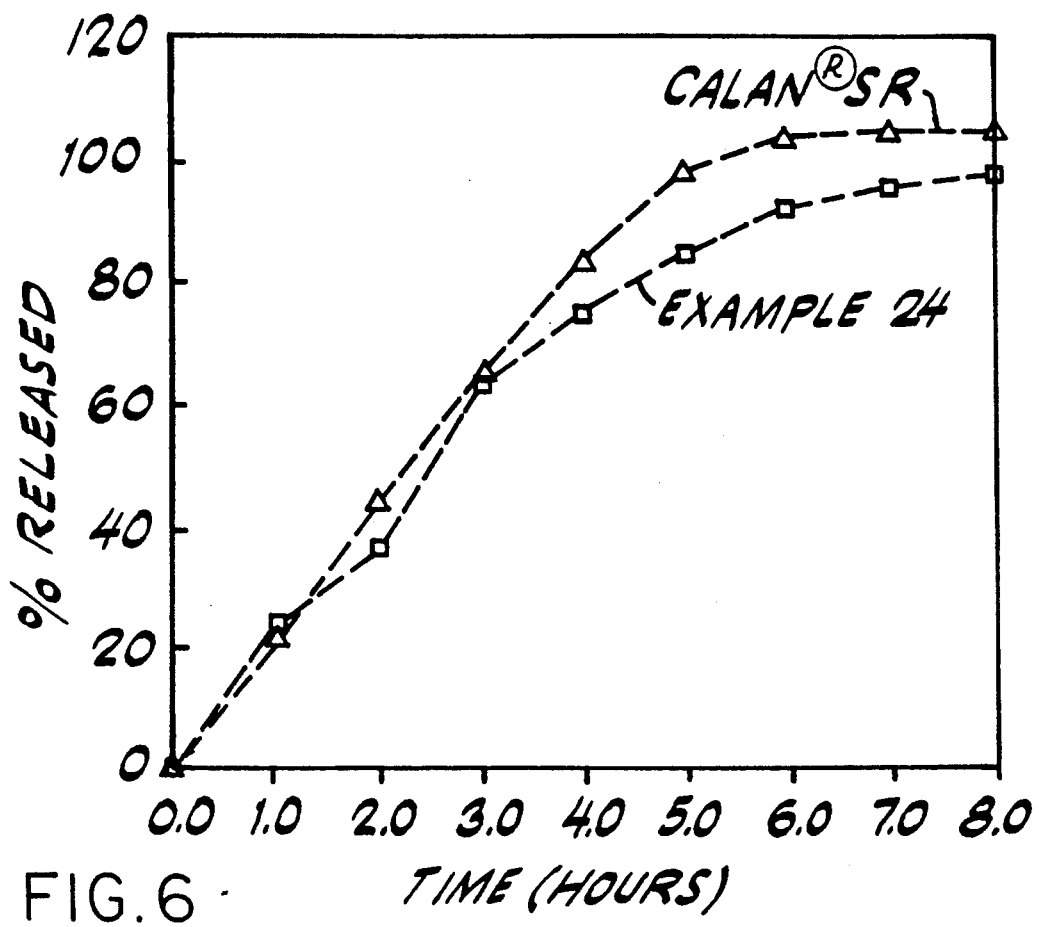
FIG. 6 is a graphical representation of the dissolution curves provided by Example 24 and Calan ® SR.

In Example 24, the excipient is then blended with the active ingredient (Verapamil HCl) and tableted according to the process set forth in Example 8. Each tablet contains about 260 mg Verapamil, about 780 mg excipient, about 21.3 mg hydrogenated vegetable oil, and about 5.3 mg magnesium stearate. The tablets are then tested for dissolution in the same manner as in Examples 11-13. As a comparative example, a Calan ® SR caplet (containing 240 mg Verapamil hydrochloride), available from G. D. Searle & Co., is similarly tested for dissolution. Further information regarding Example 14 is provided in Table 5 below, and the dissolution curves for Example 24 and Calan ® SR are provided in FIG. 6.

TABLE 5

| Example | Drug:Gum Ratio | % Gum in Excipient | LBG:XG Ratio | T50 | T90 |
|---|---|---|---|---|---|
| 18 | 1:0.09 | 50 | 1:1 | 2.4 | 5.9 |
| Calan ® | — | — | — | 2.3 | 4.5 |

EXAMPLE 25

A controlled release excipient is prepared according to procedures set forth in Example 1. The excipient of Example 25 includes dextrose as the inert pharmaceutical filler, and xanthan gum/locust bean gum in a 1:1 ratio. The percentage of dextrose as compared to the total weight of the controlled release excipient in Example 25 is 70 percent by weight.

The excipient of Example 25 is then blended with Verapamil HCl for two minutes in a high speed mixer/granulator with impeller and chopper on. Thereafter, about 15% distilled water is added to the powder mix and the mix is granulated for about 2 minutes with impeller and chopper on.

The mixed product, which is now in the form of granules, is removed from the granulator and dried in a fluid bed dryer for about 20 minutes. The dried granulation is then passed through a 20 mesh screen.

The controlled release excipient/verapamil mixture is then blended with 2% homogenated vegetable oil for about 5 minutes in a V-blender, and then 0.5% magnesium stearate is added and the mixture is blended for an additional 5 minutes. The final composition of the mixture is about 97.5% of the controlled release excipient/verapamil mixture, 2.00% homogenated vegetable oil, and 0.5% magnesium stearate, by weight.

The mixture is then compressed to form bisected, capsule-shaped punches such that the tablets have an average length of 19 mm, a width of 7 mm, and a thickness of 6 mm. The average weight of the tablets produced is about 710 mg, and the average tablet hardness is about 12.5 kp. Each tablet contains about 240.0 mg Verapamil HCl, 452.27 mg controlled release excipient (about 135.68 mg of which comprises xanthan gum/locust bean gum in a 1:1 ratio), 14.20 mg hydrogenated vegetable oil, and 3.55 mg magnesium stearate. Further information concerning the tablets of Example 25 are provided in Table 6 below:

TABLE 6

CONTROLLED RELEASE VERAPAMIL TABLET FORMULATION

| Ingredient | Percentage | Amount (mg) |
|---|---|---|
| controlled release excipient | 63.70 | 452.27 |
| Verapamil HCl | 33.80 | 240.00 |
| hydrogenated vegetable oil | 2.00 | 14.20 |
| Magnesium stearate | 0.50 | 3.55 |
| | 100% | 710 mg |

Figure 7:
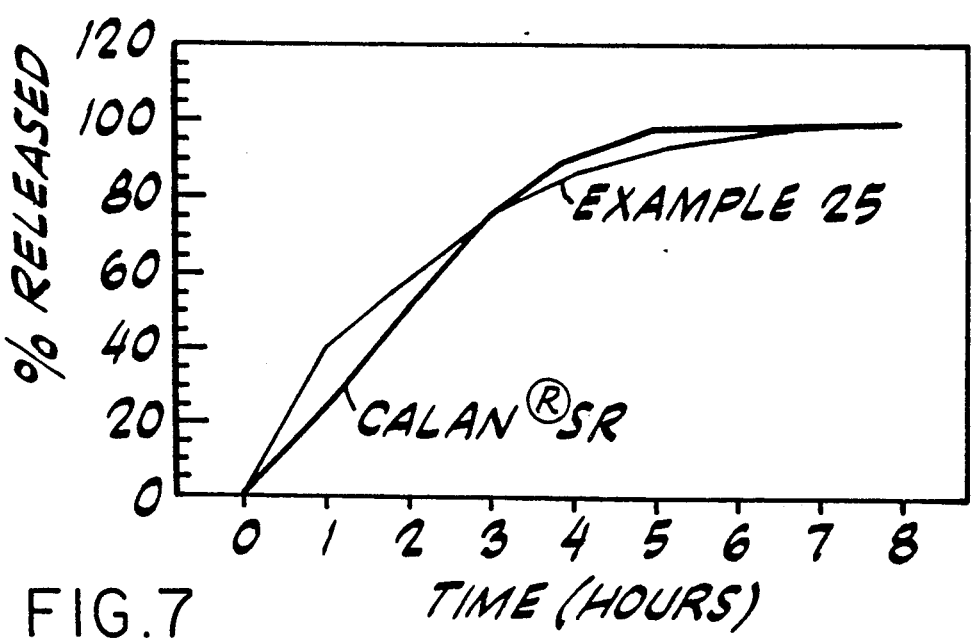
FIG. 7 is a graphical representation of the dissolution curves provided by Example 25 and Calan ® SR.

The tablets are tested in an automated USP dissolution apparatus, using distilled water at a volume of 1 liter and paddle method at 50 R.P.M. Representative dissolution curves for the tablets of Example 25 and Calan ® SR are provided in FIG. 7.

Thus, the tablets of Example 25 provide a substantially identical dissolution profile as compared to Calan ® SR. It is noteworthy, however, that the tablets of Example 25 weigh on the average of 710 mg as compared to the 1066 mg of the tablets of Example 24, which also provided a substantially identical dissolution profile as compared to Calan ® SR. It would therefore be obvious to one skilled in the art that different sized tablets having substantially identical dissolution profile as compared to Calan ® SR may be obtained by manipulating the percent hydrophilic material in the controlled release excipient, and/or by manipulating the drug to gum ratio, and/or by manipulating the method of incorporation of the verapamil. Such formulations are considered to be within the scope of the appended claims.

The preceding theories are offered solely by way of explanation and it is not intended that the invention be limited to these theories. The examples provided above are not meant to be exclusive. Many other variations of the present invention would be obvious to those skilled in the art, and are contemplated to be within the scope of the appended claims.

What is claimed is:

1. A tablet for the controlled release of verapamil in the gastro-intestinal tract, comprising:
   a controlled release excipient comprising a hydrophilic gum matrix comprising a xanthan gum and locust bean gum in a ratio of from about 3:1 to about 1:3, and an inert diluent selected from the group consisting of a monosaccharide, a disaccharide, a polyhydric alcohol, and mixtures thereof, the ratio of said inert diluent to said hydrophilic gum matrix being from about 4:1 to about 0.67:1; and an effective amount of verapamil to render a desired therapeutic effect, the ratio of verapamil to said hydrophilic gum matrix being from about 3:1 to about 1:3.

2. The tablet of claim 1, wherein the verapamil is dry granulated with said controlled release excipient prior to tableting.

3. The tablet of claim 1, wherein the verapamil is wet granulated with said controlled release excipient prior to tableting.

4. The tablet of claim 1, wherein a first portion of the verapamil is dry granulated with a first portion of said controlled release excipient, and a second portion of the verapamil is wet granulated with a second portion of said controlled release excipient, said dry granulated portion and said wet granulated portion being combined prior to tableting.

5. The tablet of claim 1, wherein the ratio of xanthan gum to locust bean gum is about 1:1.

6. A tablet for the controlled release of verapamil in the gastro-intestinal tract, comprising:
   from about 45 to about 70 percent of a controlled release excipient comprising from about 25 to about 55 percent of a hydrophilic gum matrix comprising a xanthan gum and locust bean gum in a ratio of about 1:1, and an inert diluent selected from the group consisting of a monosaccharide, a disaccharide, a polyhydric alcohol, and mixtures thereof; and an effective amount of verapamil to render a desired therapeutic effect.

7. The tablet of claim 6, wherein the ratio of verapamil to said hydrophilic material is from about 1.0:0.4 to about 1.0:0.7.

8. A method for preparing a controlled release verapamil formulation, comprising:
   preparing a hydrophilic gum matrix comprising xanthan gum and locust bean gum in a ratio of about 1:1;
   mixing said hydrophilic gum matrix with an inert diluent selected from the group consisting of a monosaccharide, a disaccharide, a polyhydric alcohol, and mixtures thereof, in a ratio of said inert diluent to said hydrophilic gum matrix from about 4:1 to about 0.67:1;
   combining the mixture of hydrophilic gum matrix/inert diluent with verapamil, such that the ratio of verapamil to said hydrophilic gum matrix/inert diluent mixture is from about 1.0:0.4 to about 1.0:0.7; and
   compressing the resultant mixture to form solid tablets having a desired dosage of verapamil to render a desired therapeutic effect, the verapamil being released according to a desired dissolution profile when exposed to gastric fluid.

9. The method of claim 8, wherein verapamil is combined with the mixture of hydrophilic gum matrix/inert diluent via wet granulation.

* * * * *